United States Patent [19]

Jones et al.

[11] Patent Number: 4,469,660
[45] Date of Patent: Sep. 4, 1984

[54] RACK FOR DEVELOPING MULTIPLE CHROMATOGRAMS

[75] Inventors: Donald W. Jones, Palm Springs; Michael J. Gabor, Mission Viejo, both of Calif.

[73] Assignee: Marion Laboratories, Kansas City, Mo.

[21] Appl. No.: 354,159

[22] Filed: Mar. 5, 1982

[51] Int. Cl.³ ............................................. G01N 31/08
[52] U.S. Cl. ..................................... 422/70; 422/104; 211/41
[58] Field of Search ..................... 436/162; 422/70, 99, 422/104; 210/658, 198.3; 211/41; 73/61.1 C

[56] References Cited

U.S. PATENT DOCUMENTS

| | | | |
|---|---|---|---|
| 3,245,546 | 4/1966 | Stuhler | 211/41 |
| 3,667,917 | 6/1972 | Brandt | 436/162 |
| 4,065,384 | 12/1977 | Pandey et al. | 210/658 |
| 4,214,292 | 7/1980 | Johnson | 211/41 |
| 4,377,641 | 3/1983 | Dee et al. | 436/162 |

OTHER PUBLICATIONS

Stahl-Thin layer Chromatography Springer Verlag, N.Y. 1980 pp. 61, 67.

Primary Examiner—Hiram H. Bernstein

[57] ABSTRACT

Means for developing a plurality of chromatograms simultaneously without prior equilibration are disclosed. When the means of the invention are used, the chromatograms are vertically positioned with their lower ends in developing fluid, their vertical edges equidistant from a solid wall member, and spacing between chromatograms to permit air flow. The means comprise a rack for use in a developing tank and in which the chromatograms are vertically supported in spaced slits, the ends of which are equidistant from a wall member when in the developing tank.

8 Claims, 6 Drawing Figures

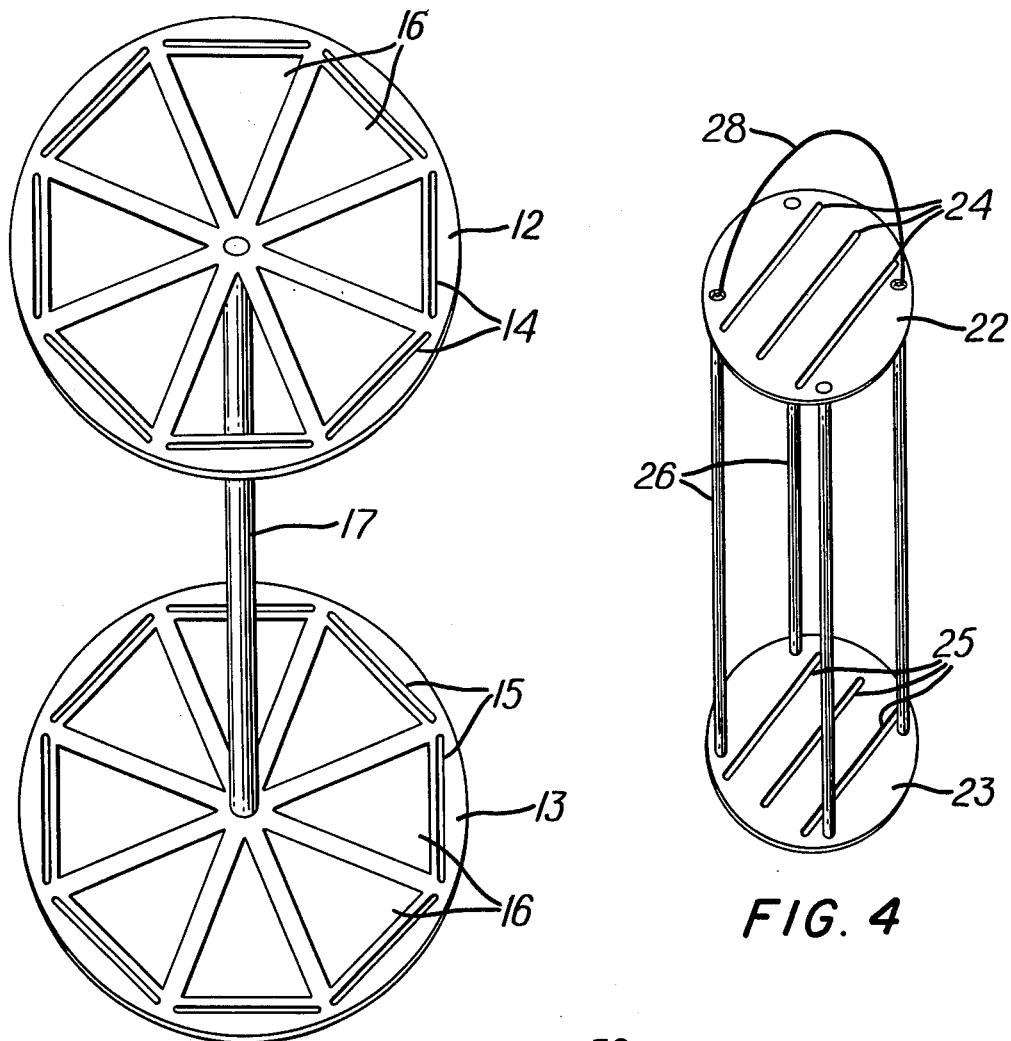
FIG. 3
FIG. 4
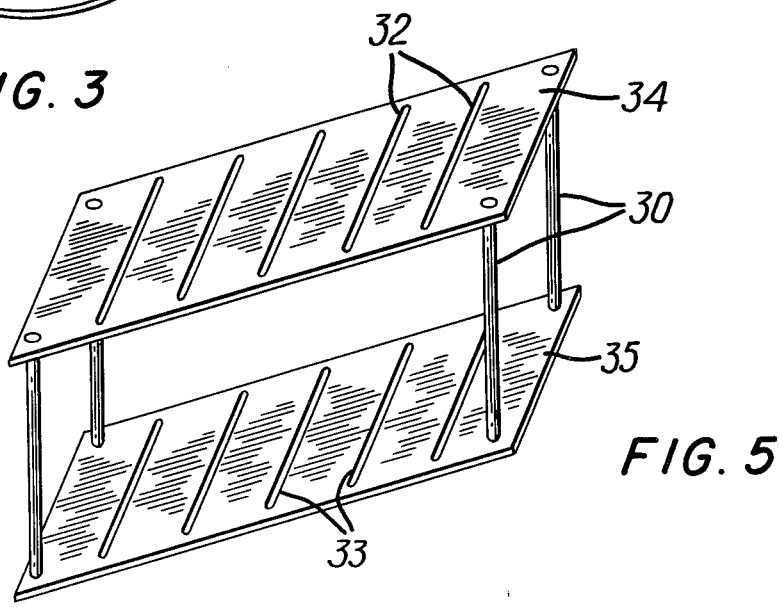
FIG. 5

RACK FOR DEVELOPING MULTIPLE CHROMATOGRAMS

BACKGROUND OF THE INVENTION

1. Field of the Invention

This invention relates to a method and means for simultaneously developing a plurality of thin layer chromatograms to achieve optimum migration without prior equilibration. The invention has particular application to thin layer chromatography as described in U.S. Pat. Nos. 3,714,035, 3,963,421, and 4,272,380.

2. State of the Art

Thin layer chromatographic analysis is commonly effected by impregnating a chromatogram with one or more substances to be analyzed and subjecting the chromatogram to a developing procedure. During the developing stage the chromatogram is placed in a developing tank containing a small amount of fluid. The fluid migrates up the chromatogram carrying with it the test materials. Following migration, the relative positions and color reactions of the test materials are determined by applying various chemicals to the chromatograms.

Since position of a test material is significant in chromatographic analysis, it is important that the test material migrate upward in a straight line and that all materials on a chromatogram migrate uniformly. Such uniform migration generally has been achieved only when single chromatograms are placed in a developing tank and/or when chromatograms are subjected to an equilibration step in the developing chamber prior to development. Equilibration involves holding the chromatograms above the fluid in the developing tank prior to lowering into the fluid.

It is frequently desirable to develop and process several chromatograms simultaneously. However, even with equilibration, uneven migration of test substances commonly occurs when more than one chromatogram is developed at the same time. Where multiple, very thin chromatograms, such as glass micro fiber chromatograms, are developed in the same tank, equilibration has not proven effective in achieving optimal migration of test substances.

It has now been discovered that a plurality of thin layer chromatograms, even very thin and relatively flexible, silicic acid impregnated glass micro fiber chromatograms, can be developed simultaneously to achieve optimum migration without prior equilibration.

SUMMARY OF THE INVENTION

This invention relates to a method and apparatus for simultaneously developing a plurality of thin layer chromatograms. The method comprises spacing the chromatograms vertically in a developing tank with both vertical edges of each chromatogram in proximity to and equidistant from a solid vertical wall member while permitting vapors from the developing fluid to circulate around the chromatograms.

The apparatus of the invention is a rack which comprises upper and lower members, which are flat, relatively thin and fit snugly into a developing tank without touching the tank's walls. The upper and lower members are held together by attachment means which hold the two members apart a distance less than the length of the chromatogram but at least as great as the length of the chromatogram's region for migration. The upper member is provided with a plurality of spaced slits which are large enough for a chromatogram to pass therethrough. The upper slits are positioned such that both ends of each will be in proximity to and equidistant from a vertical solid wall member when the rack is in the developing rank. The lower member is provided with slits which are positioned directly below and in line with the slits in the upper member. The slits in the lower member are large enough to allow an end of a chromatogram to pass therethrough, but not large enough to allow the chromatogram to pass completely through. In preferred practice, the upper and lower members are provided with holes between the slits to facilitate vapor flow in the developing tank.

BRIEF DESCRIPTION OF THE DRAWINGS

FIG. 3 is a perspective view of the rack of the invention having slits disposed about the circumference of circular upper and lower members.

FIG. 4 is a perspective view of the rack of the invention having parallel slits in circular upper and lower members.

FIGS. 5 and 6 depict rectangular racks of the invention having transverse slits.

DETAILED DESCRIPTION OF THE INVENTION

Figure 1:
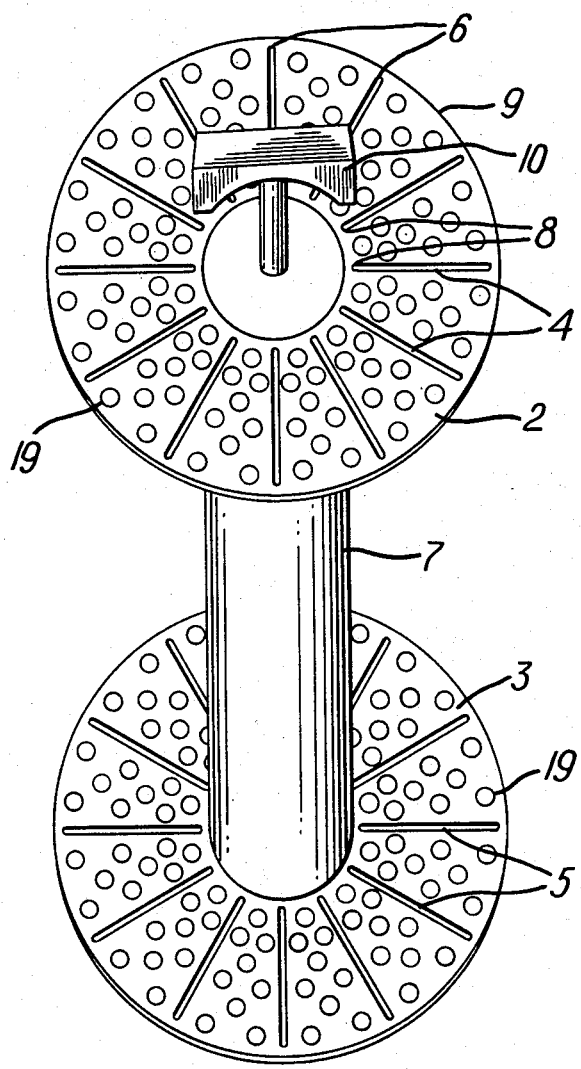
FIGS. 1 and 2 are perspective views of the rack of the invention having circular upper and lower members and radially spaced slits.

This invention provides a rack and method for developing multiple thin layer chromatographs simultaneously in a single developing tank without prior equilibration. By means of the invention, it is possible to rapidly develop a number of thin layer paper chromatograms. The invention has particular utility in simultaneous development of three or more chromatograms.

In the practice of the method of the invention, a plurality of chromatograms are vertically positioned in a developing tank such that the vertical edges of each chromatogram are near but do not touch a solid that is, non-permeable, vertical wall surface or member. Both vertical edges of a given chromatogram are substantially the same distance from a vertical wall member. The chromatograms must be positioned a sufficient distance apart to allow ready air flow around each chromatogram. Generally it is desirable to allow each chromatogram to occupy a space equal to at least thirteen times its own volume. Five millimeters separation is generally adequate for glass micro fiber chromatograms.

When the chromatograms are positioned in the above manner, they may be immediately lowered into a developing fluid, without prior equilibration. Developing can be effected by simply holding the chromatograms so positioned in the developing fluid and allowing the fluid to migrate according to conventional techniques.

Optimally, in the practice of this invention, each chromatogram is positioned identically to every other chromatogram in the tank. That is, for optimal practice of the invention, each individual chromatogram is not only placed so that both edges are exposed to a uniform environment, but also all chromatograms are exposed to substantially the same environment.

The present invention also provides racks with which the method of the invention can be practiced. The racks of the invention support a plurality of chromatograms in a manner which permits direct development that is, development without equilibration. Although the racks are hereinafter described with reference to the specific embodiments depicted in the drawings, it is to be understood that any rack which provides means for supporting a plurality of chromatograms in the manner required by the method of the invention is within the invention.

Broadly stated, the developing racks of the invention comprise flat relatively thin, upper and lower members having slits and of a configuration, such that they fit fairly closely into a developing tank without touching the walls of the tank. The upper and lower members may be made of any relatively rigid material which does not react with the developing reagents. Examples include stainless steel and polypropylene. The members are attached to one another by means which hold the members apart.

The spacing between the members is dependent upon the size of the chromatogram employed. Generally, the entire region which is observed during chromatographic analysis should be between the two members. Thus, the members should be spaced at least the full length of the region for migration. On the other hand, the members must be close enough together to support the ends of a chromatogram. Thus, the spacing must not exceed the length of the chromatogram.

The members are slitted in order to permit insertion and support of the chromatograms. The upper member has slits which are of a size sufficient to allow easy insertion of a chromatogram, while holding the chromatogram substantially vertical. Their length should not be substantially greater than the width of the chromatograms in order to insure relatively precise placement of the chromatograms.

The lower member has slits which will receive the lower ends of the chromatograms and support them while the rack is being transferred to the developing tank after it has been loaded with chromatograms. A chromatogram, the lower end of which is slightly narrower than the body or a chromatrogram having a slightly widened portion above its lower end can be supported in a slit having a length less than the wider body portion of the chromatogram.

The slits in the upper member are positioned such that the ends thereof will be in proximity to and equidistant from a solid vertical wall member when in the developing tank. Further the slits are spaced in order to permit air flow around the chromatograms. Preferably the spacing is uniform and provides a symmetrical pattern of slits. The slits in the lower member are positioned below and in line with the slits in the upper member so that when a chromatogram is inserted it will be held in a substantially vertical position. In most preferred form both upper and lower members of the rack of the invention are provided with a plurality of holes or openings which facilitate air and vapor flow. Optimally these holes are uniformly positioned between each slit.

Referring now to the drawings, FIG. 1 depicts the preferred embodiment of the invention. In this embodiment, circular upper member 2 and circular lower member 3 are provided with radially spaced slits 4 and 5 respectively and are attached by core 7. Core 7 is substantial enough in dimensions to serve as a wall member. Slits 4 are identical and are placed such that the distance between core 7 and ends 8 is substantially the same as the distance between rim 9 of upper member 2 and ends 6. Slits 5 are identical to one another and are aligned with slits 4. Upper and lower members 2 and 3 are additionally provided with holes 9 which facilitate air flow. Handle 10 may be attached to upper member 2 to permit easy insertion and removal of the rack from a developing tank.

Figure 2:
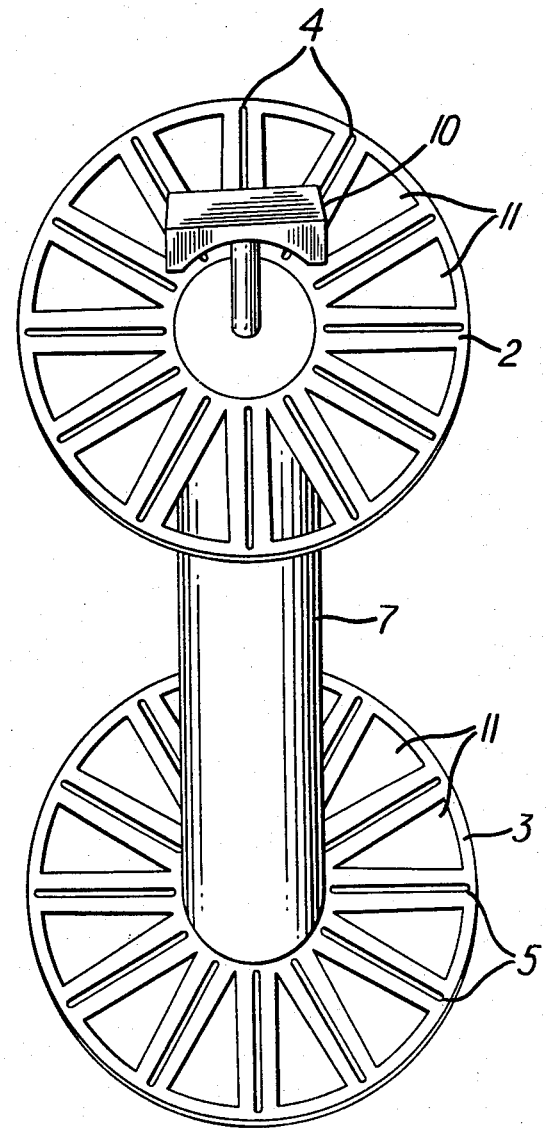

In the most preferred embodiment for use with silicic acid impregnated glass micro fiber paper chromatograms, which are 114 mm long and 41 mm wide and have small cut out notches along their lower vertical edges upper and lower members 2 and 3 are 5½ inches in diameter. Twelve slits 4 are spaced evenly around a 54 mm diameter circle. Slits 4 are 3 mm wide×43 mm long while slits 5 are 3 mm wide and 40 mm long. Core 7 is 1⅞" in diameter and 4" high. FIG. 2 is identical to the preferred form of FIG. 1 except that holes 11 cover a substantial area of members 2 and 3.

FIG. 3 is a rack having upper and lower members 12 and 13 around the circumference of which slits 14 and 15 respectively are evenly spaced. Members 12 and 13 are provided with holes 16 while rod 17 supports members 12 and 13 in spaced relationship.

FIG. 4 is provided with circular upper and lower members 22 and 23 in which three spaced parallel slits 24 and 25 are disposed across their diameters. Handle 28 permits easy insertion and removal from the developing tanks while rods 26, placed at equidistant positions about the circumferences of members 22 and 23, support them in spaced relationship.

Figure 6:
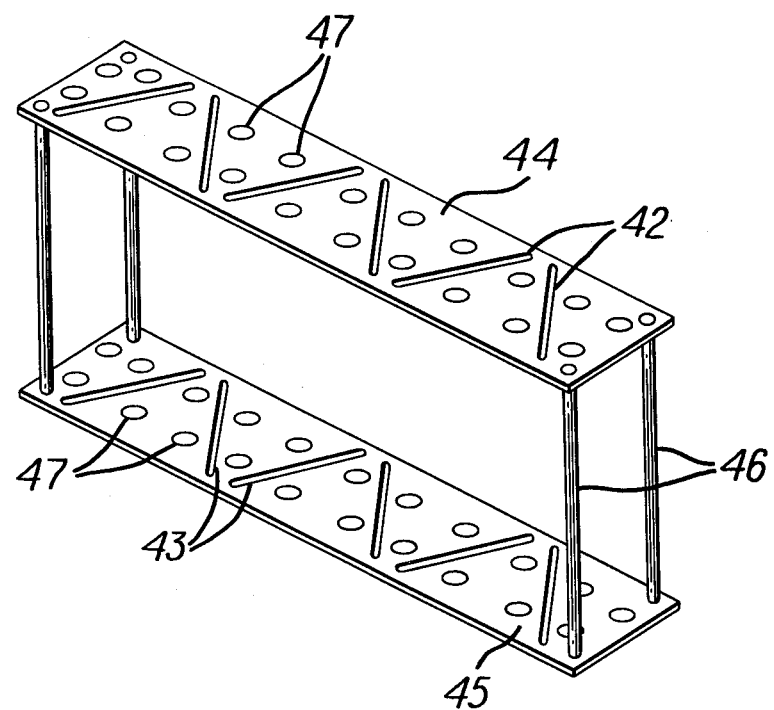

In FIG. 5 slits 32 and 33 are spaced at equidistant intervals and perpendicular to the longitudinal axis of rectangular upper and lower members 34 and 35 which in turn are supported by rods 36. In FIG. 6 slits 42 and 43 are symmetrically positioned at angles along the longitudinal axis of rectangular members 44 and 45. Members 44 and 45 are held in spaced relationship by rods 46 placed at their corners and are provided with holes 47 for ventilation.

We claim:

1. A rack for supporting a plurality of chromatograms in a developing tank comprising:

flat thin upper and lower members, said members having a shape and size such that they fit closely into the developing tank without touching the tank's walls; said members being attached to one another by attachment means which hold the members apart a distance which is less than the length of the chromatograms but at least as long as the migratory region of the chromatograms; said upper member being provided with a plurality of spaced slits which are of a size sufficient to loosely receive a chromatogram, each upper slit positioned such that its ends are equidistant from a solid vertical wall member when the rack is in the developing tank; said lower member being provided with the same number of slits as said upper member, said lower slits being of a size sufficient to loosely receive and support the lower end of the chromatograms and being positioned below and in line with said upper slits.

2. The rack of claim 1 wherein the upper and lower members are provided with a plurality of holes.

3. The rack of claim 1 wherein the upper and lower members are circular.

4. The rack of claim 3 wherein the slits are radially spaced symmetrically about a solid core, said core being the attachment means and being a wall member.

5. The rack of claim 4 wherein the upper and lower members are provided with a plurality of holes between the slits to facilitate air flow.

6. The rack of claim 3 having three parallel slits spaced across the diameters of the upper and lower members.

7. The rack of claim 3 wherein the slits are evenly spaced about the circumference of the upper and lower members.

8. The rack of claim 1 wherein the upper and lower members are rectangular and the slits are positioned transversely.

* * * * *

UNITED STATES PATENT AND TRADEMARK OFFICE
CERTIFICATE OF CORRECTION

PATENT NO. : 4,469,660
DATED : September 4, 1984
INVENTOR(S) : Donald W. Jones and Michael J. Gabor It is certified that error appears in the above-identified patent and that said Letters Patent is hereby corrected as shown below:

IN THE SPECIFICATION

Col. 4, line 1, "holes 9" should read --holes 19--.

Col. 4, line 31, "rods 36" should read --rods 30--.

Signed and Sealed this

Ninth Day of April 1985

[SEAL]

Attest:

DONALD J. QUIGG

Attesting Officer     Acting Commissioner of Patents and Trademarks